United States Patent [19]

Kim et al.

[11] 4,345,085

[45] Aug. 17, 1982

[54] METHOD FOR PREPARING 2-PYRAZOLIN-5-ONES FROM 1,2,4-OXADIAZOLES

[75] Inventors: Chang Kyu Kim; Cataldo A. Maggiulli; Paul A. Zielinski, all of Rochester, N.Y.

[73] Assignee: Eastman Kodak Company, Rochester, N.Y.

[21] Appl. No.: 220,409

[22] Filed: Dec. 29, 1980

[51] Int. Cl.³ .................. C07D 231/52; C07D 407/12
[52] U.S. Cl. ..................................... 548/360; 548/131
[58] Field of Search ........................................ 548/360

[56] References Cited

U.S. PATENT DOCUMENTS

| | | | |
|---|---|---|---|
| 2,600,788 | 6/1952 | Loria et al. | 430/386 |
| 2,865,748 | 12/1958 | Feniak et al. | 430/386 |
| 3,062,653 | 11/1962 | Weissberger et al. | 430/554 |
| 3,419,391 | 12/1968 | Young | 430/387 |
| 3,927,025 | 12/1975 | Korbonits | 548/362 |

OTHER PUBLICATIONS

Boulton et al., J. Chem. Soc. (London), C, 1967, (20), pp. 2005–2007.
Ruccia et al., *A New Rearrangement in the 1,2,4-Oxadiazole Series,* J. Chem. Soc., Chem. Comm. (1970), p. 866.

*Primary Examiner*—Henry R. Jiles
*Assistant Examiner*—Natalia Harkaway
*Attorney, Agent, or Firm*—D. F. Janci

[57] ABSTRACT

A method for preparing 2-pyrazolin-5-ones from 1,2,4-oxadiazoles is described. The method comprises forming a liquid reaction system of a base catalyst and a 1,2,4-oxadiazole in an organic liquid reaction medium and heating the reaction system to a temperature sufficient to cause the 1,2,4-oxadiazole to be rearranged to a 2-pyrazolin-5-one.

14 Claims, No Drawings

METHOD FOR PREPARING 2-PYRAZOLIN-5-ONES FROM 1,2,4-OXADIAZOLES

BACKGROUND OF THE INVENTION

1. Field of the Invention

This invention relates to a method for preparing 2-pyrazolin-5-ones. More particularly this invention concerns a method for preparing 2-pyrazolin-5-ones from 1,2,4-oxadiazoles. In one aspect this invention relates to a process for preparing 2-pyrazolin-5-ones that are particularly useful as color forming couplers or as intermediates in preparing color forming couplers which produce dyes in photographic elements.

2. Description Relative to the Prior Art

It is well known in the photographic art that 2-pyrazolin-5-ones represented by the structural formula

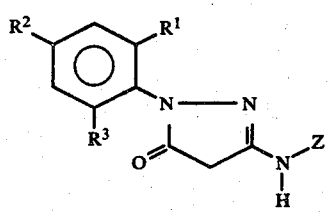

(wherein each of $R^1$, $R^2$ and $R^3$ is hydrogen, halo, alkyl, or alkoxy, and Z is an alkyl, acyl or aryl radical) are useful as color forming couplers or as intermediates in preparing color forming couplers useful for producing dyes in photographic elements. Many references describe the use of such 2-pyrazolin-5-ones in photographic elements and also describe methods for synthesizing such compounds. See, for example, U.S. Pat. Nos. 3,419,391; 3,062,653; 2,865,748; 2,600,788; and the patents referenced therein, all of which are hereby incorporated herein by reference.

It would be desirable to have a new synthetic route to 2-pyrazolin-5-ones which is more efficient and more economical than the previously known methods. The present invention unexpectedly provides such a synthetic route. It involves the rearrangement of certain 1,2,4-oxadiazole to their corresponding 2-pyrazolin-5-ones.

In general regard to oxadiazole rearrangements, U.S. Pat. No. 3,927,025, to Korbonits et al, and Ruccia et al, *A New Rearrangement in the 1,2,4-Oxadiazole Series*, in J. Chem. Soc. Chem. Comm., p. 866 (1970) are relevant references. These references describe rearrangements of 1,2,4-oxadiazoles, but the rearrangements described are carried out in aqueous solutions and yield pyrazolines or triazolinones, which are, chemically, compounds significantly different from 2-pyrazolin-5-ones. These references do not describe or suggest any new synthetic routes to 2-pyrazolin-5-ones.

SUMMARY OF THE INVENTION

The invention provides a method for preparing 2-pyrazolin-5-ones, which method comprises forming a liquid reaction system comprising an organic liquid reaction medium, a base catalyst, and at least one 1,2,4-oxadiazole represented by the structural formula

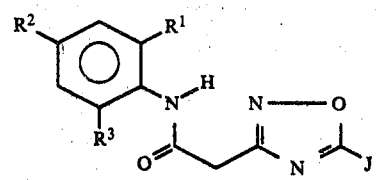

and heating the reaction system to a temperature sufficient to cause the 1,2,4-oxadiazole to be rearranged to its corresponding 2-pyrazolin-5-one.

In the formula above: each of $R^1$, $R^2$ and $R^3$ is hydrogen, halo, alkyl having from 1 to 5 carbon atoms, or alkoxy having from 1 to 5 carbon atoms; and J is alkyl having from 1 to 20 carbon atoms, phenoxyalkyl with the alkyl portion thereof having from 1 to 20 carbon atoms, phenyl, alkoxyphenyl, a 5-membered aromatic heterocyclic radical, phenoxyacylaminophenyl, or phenoxyalkyl substituted with one or more nitro radicals in at least one of the para or ortho positions.

The method of the present invention is more efficient (producing higher yields) and more economical than previously known methods of synthesizing 2-pyrazolin-5-ones.

DETAILED DESCRIPTION OF THE PREFERRED EMBODIMENTS

The 1,2,4-oxadiazole starting materials for the method of this invention are conveniently prepared by known methods. For example, 2-(5-methyl-1,2,4-oxadiazol-3-yl)-2',4',6'-trichloroacetanilide is prepared by the following reaction sequence:

First, 2,4,6-trichloroaniline is converted to 2-chloro-2',4',6'-trichloroacetanilide in 92–95 percent yield by heating with chloroacetyl chloride under reflux for 3 hours in an aromatic hydrocarbon solvent such as toluene or xylene, i.e.,

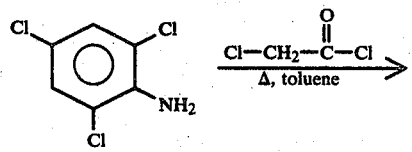

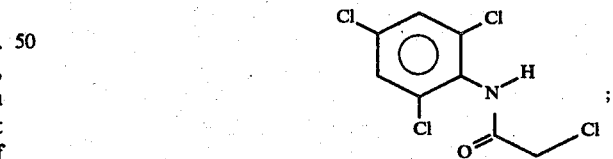

The resulting compound is then reacted with sodium cyanide in water and N,N-dimethylformamide (DMF) at room temperature for 18 hours to give 2-cyano-2'-4'-6'-trichloroacetanilide in 93–95 percent yield, i.e.,

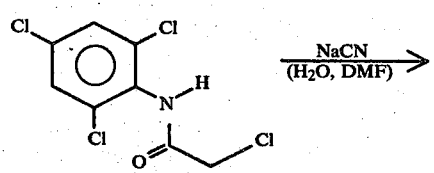

-continued

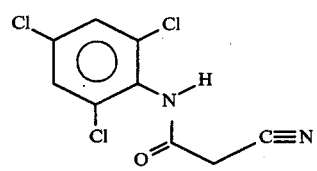

The product is heated next with hydroxylamine in aqueous ethanol under reflux for 45 minutes to obtain 3-oxo-3-(2,4,6-trichloroanilino)propionamidoxime in 86 percent yield, i.e.,

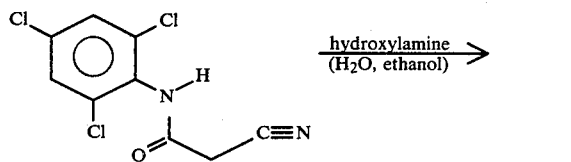

The amidoxime is then converted to the 1,2,4-oxadiazole in 95 percent yield by stirring with acetic anhydride in acetic acid at room temperature for 2 hours and then heating under reflux for 1.5 hours, i.e.,

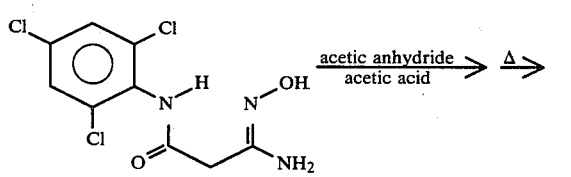

The method of the invention is then used to convert the 1,2,4-oxadiazole to the 2-pyrazolin-5-one. As previously described, the method comprises forming a liquid reaction system of a base catalyst and the 1,2,4-oxadiazole in an organic liquid reaction medium and heating the reaction system to a temperature sufficient to cause the 1,2,4-oxadiazole to be rearranged to the 2-pyrazolin-5-one, e.g., heating a solution of potassium hydroxide and 2-(5-methyl-1,2,4-oxadiazol-3-yl)-2',4',6'-trichloroacetanilide in anhydrous ethanol under reflux at a temperature of 80° C. for 8 to 14 hours to yield 3-acetamido-1-(2,4,6-trichlorophenyl)-2-pyrazolin-5-one, i.e.,

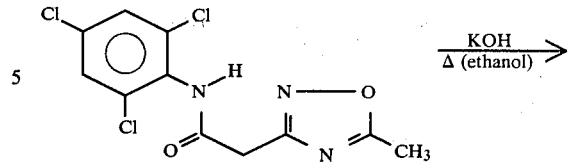

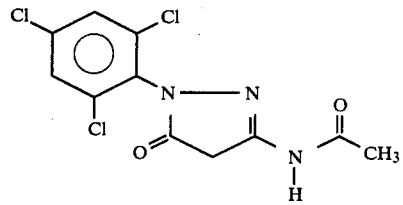

As illustrated in Example 1 below, the method of the invention produces significant yields of the desired 2-pyrazolin-5-one when carried out in an organic medium. In contrast, insignificant yields (in a commercial sense) are obtained when the rearrangement is attempted in an aqueous medium. By "liquid reaction system" we mean a solution or dispersion of the 1,2,4-oxadiazole and base catalyst in an organic liquid reaction medium. In other words, the system is substantially non-aqueous or anhydrous.

The base catalyst is included in the reaction system in an effective catalytic amount and can be chosen from any of the well known base catalysts. Examples of base catalysts useful in the method are alkali hydroxides, alkali alkoxides, alkali triphosphates, and alkali carbonates. Specific examples of such base catalysts are potassium hydroxide, sodium methoxide, and potassium carbonate.

The yields obtainable by the method of the invention are somewhat dependent upon the organic liquid reaction medium included in the reaction system and the temperature at which the reaction is carried out. The reaction is essentially a competition between the rearrangement and solvolysis. Higher temperatures and/or organic liquid media which are aprotic solvents will favor the rearrangement over solvolysis and, thus, increase the yield. Generally, a temperature of from about 80° C. to about 125° C. will produce significant yields. A temperature of at least 80° C. in a protic organic solvent (i.e., an organic solvent having acidic hydrogen atoms, such as a hydrogen atom attached to a nitrogen or oxygen atom, e.g., ethanol or methanol) will give yields usually greater than 40 percent. Using a protic solvent with a higher boiling point (e.g., 2-methoxyethanol, b.p. 124° C.) will enable the reaction to be carried out at a higher temperature (e.g., approximately 125° C.) and give yields usually higher than about 70 percent. An aprotic solvent (i.e., a polar solvent of moderately high dielectric constant having no acidic hydrogens, e.g., N,N-dimethylformamide [DMF]) is preferred, because it inherently has less tendency toward solvolysis. Yields approaching 90 percent are achievable by using an aprotic organic solvent as the reaction medium.

In embodiments of the invention using an oxadiazole having the formula set out in the Summary of the Invention wherein J is a nitrophenoxyalkyl radical, the initial rearrangement proceeds further, spontaneously, to undergo what is generally referred to as a Smiles rearrangement. An embodiment involving the Smiles rearrangement is illustrated in Example 19 below.

The following Examples further illustrate preferred embodiments of the practice of the invention.

Examples 1–19 illustrate the method of the invention as practiced on 1,2,4-oxadiazoles to produce 2-pyrazolin-5-ones.

EXAMPLE 1

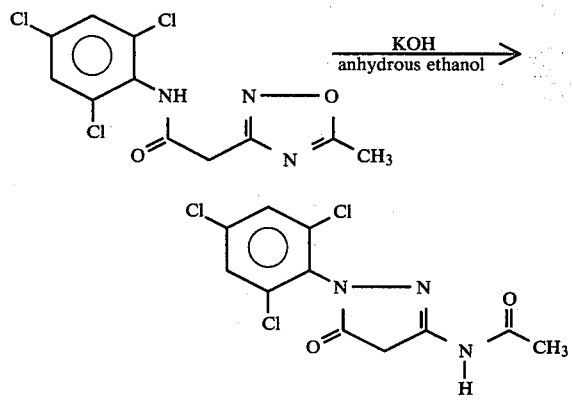

EXAMPLES 2-6

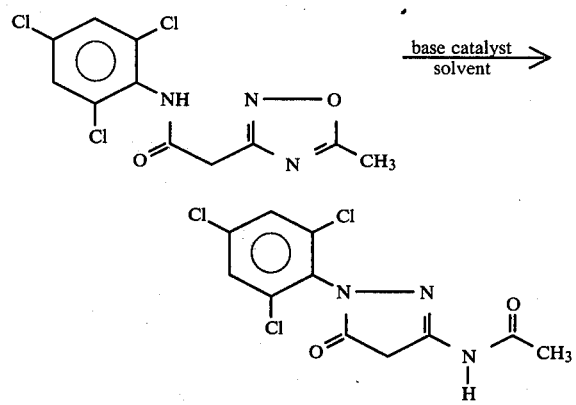

The above base-catalyzed rearrangement of 2-(5-methyl-1,2,4-oxadiazol-3-yl)-2',4',6'-trichloroacetanilide to 3-acetamido-1-(2,4,6-trichlorophenyl)-2-pyrazolin-5-one was run under several different reaction conditions. The results are summarized in the following Table I.

TABLE I

| Example No. | Base Catalyst | Organic Liquid Reaction Medium | Reaction Temperature | Reaction Time | Percent Yield of the 2-Pyrazolin-5-one |
|---|---|---|---|---|---|
| 2 | sodium methoxide | anhydrous ethanol | 80° C. | 16 hrs. | 44 |
| 3 | sodium methoxide | 2-methoxyethanol (methyl cellosolve) | 125° C. | 3 hrs. | 74 |
| 4 | sodium methoxide | N,N-dimethylformamide (DMF) | 110° C. | 2 hrs. | 80 |
| 5 | potassium carbonate | DMF | 110° C. | 2 hrs. | 80 |
| 6 | potassium hydroxide | DMF | 110° C. | 2 hrs. | 75 |

To a solution of 10 g of potassium hydroxide in 200 ml of anhydrous ethanol was added 20 g of 2-(5-methyl-1,2,4-oxadiazol-3-yl)-2',4',6'-trichloroacetanilide. The mixture was heated under reflux for 10 hours. After it cooled, the mixture was acidified with 20 ml of acetic acid and concentrated to almost dryness under reduced pressure. The residue was slurried in water, collected, and dried. The crude product was stirred with 200 ml of hexane for 15 min., and the hexane solution was separated in hot ethanol and allowed to crystallize over night. There was obtained 9.6 g (48%) of 3-acetamido-1-(2,4,6-trichlorophenyl)-2-pyrazolin-5-one, mp 234°–235.5° C., and 1.5 g (12%) of 2,4,6-trichloroaniline.

The procedure was repeated using a mixture of 20% water and 80% ethanol as the solvent instead of the anhydrous ethanol used above. This time the yield of 3-acetamido-1-(2,4,6-trichlorophenyl)-2-pyrazolin-5-one was very poor, i.e., only 8%, while a 57% yield of 2,4,6-trichloroaniline was obtained. This illustrates that, in contrast to the excellent yields produced in an organic medium, very poor yields are obtained when the rearrangement is run in an aqueous medium.

EXAMPLE 7

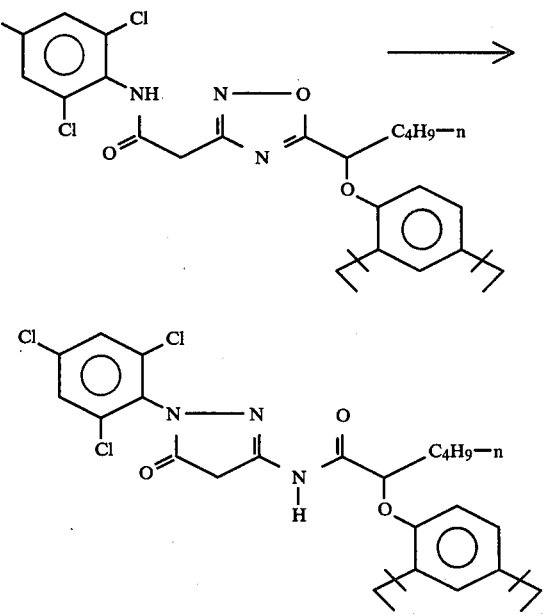

To a solution of 2.2 g of potassium hydroxide in 100 ml of anhydrous ethanol was added 10 g of 2-{5-[1-(2,4-di-tert.-pentylphenoxy)pentyl]-1,2,4-oxadiazol-3-yl}-

2',4',6'-trichloroacetanilide. The mixture was heated under reflux for 2½ hrs. After it was cooled, the mixture was acidified with 3 ml of acetic acid and ethanol was evaporated under reduced pressure. The residual oil was taken up into 100 ml of toluene, washed with water, dried over anhydrous magnesium sulfate, and evaporated to dryness under reduced pressure. The residual yellow oil was crystallized from hexane. There was obtained 8.9 g (89%) of 3-[2-(2,4-di-tert.-pentylphenoxy)hexanoylamido]-1-(2,4,6-trichlorophenyl)-2-pyrazolin-5-one as colorless crystals, mp 98°–100° C.

EXAMPLES 8-17

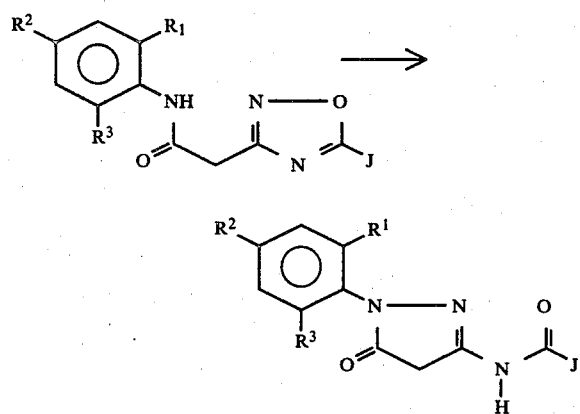

The following list of examples illustrates additional preparations of 1-aryl-3-acylamido-2-pyrazolin-5-ones according to the above equation using a procedure similar to that described in Example 7. In each example, starting material, base/solvent, reaction temperature/reaction time, product, its melting point and yield are listed in order.

EXAMPLE 8

2-{5-[1-(m-Pentadecylphenoxy)propyl]-1,2,4-oxadiazol-3-yl}-2',4',6'-trichloroacetanilide($R^1=R^2=R^3=Cl$,

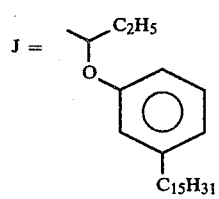

KOH/EtOH, reflux/2 hrs., 3-[2-(m-pentadecylphenoxy)butyramido]-1-(2,4,6-trichlorophenyl)-2-pyrazolin-5-one, mp 131°–132° C., 85%.

EXAMPLE 9

2-{5-[1-(m-Pentadecylphenoxy)propyl]-1,2,4-oxadiazol-3-yl}-2'-chloro-4',6'-dimethylacetanilide ($R^1=Cl$, $R^2=R^3=CH_3$—,

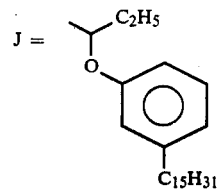

KOH/MeOH, reflux/2½ hrs., 1-(2-chloro-4,6-dimethylphenyl)-3-[2-(m-pentadecylphenoxy)butyramido]-2-pyrazolin-5-one, mp 93°–97° C., 77%.

EXAMPLE 10

2-(5-Methyl-1,2,4-oxadiazol-3-yl)acetanilide ($R^1=R^2=R^3=H$, $J=CH_3$—), KOH/EtOH, reflux/4½ hrs., 3-acetamido-1-phenyl-2-pyrazolin-5-one, mp 207°–213° C. (dec.), 42%.

EXAMPLE 11

2-(5-Methyl-1,2,4-oxadiazol-3-yl)-4'-methoxyacetanilide ($R^1=R^3=H$, $R^2=CH_3O$—, $J=CH_3$), KOH/MeOH, reflux/4 hrs., 3-acetamido-1-(p-methoxyphenyl)-2-pyrazolin-5-one, mp 234°–236° C., 24%.

EXAMPLE 12

2-(5-Ethyl-1,2,4-oxadiazol-3-yl)-2',4',6'-trichloroacetanilide ($R^1=R^2=R^3=Cl$, $J=CH_3CH_2$—), KOH/EtOH, refux/8 hrs., 3-propionamido-1-(2,4,6-trichlorophenyl)-2-pyrazolin-5-one, mp 167°–170.5° C., 42%.

EXAMPLE 13

2-(5-n-Propyl-1,2,4-oxadiazol-3-yl)-2',4',6'-trichloroacetanilide ($R^1=R^2=R^3=Cl$, $J=CH_3CH_2CH_2$—), KOH/EtOH, reflux/8 hrs., 3-butyramido-1-(2,4,6-trichlorophenyl)-2-pyrazolin-5-one, mp 153°–158° C., 44%.

EXAMPLE 14

2-(5-tert.-Butyl-1,2,4-oxadiazol-3-yl)-2',4',6'-trichloroacetanilide ($R^1=R^2=R^3=Cl$, $J=(CH_3)_3C$—, KOH/EtOH, reflux/5 hrs., 3-pivaloylamido-1-(2,4,6-trichlorophenyl)-2-pyrazolin-5-one, mp 182°–186° C., 69%.

EXAMPLE 15

2-(5-Phenyl-1,2,4-oxadiazol-3-yl)-2',4',6'-trichloroacetanilide ($R^1=R^2=R^3=Cl$, J=ph), KOH/EtOH, reflux/10 hrs., 3-benzoylamido-1-(2,4,6-trichlorophenyl)-2-pyrazolin-5-one, mp 278°–280° C., 62%.

EXAMPLE 16

2-[5-(p-Methoxyphenyl)-1,2,4-oxadiazol-3-yl]-2',4',6'-trichloroacetanilide ($R^1=R^2=R^3=Cl$, $J=$p-$CH_3O$—$C_6H_4$—), KOH/EtOH, reflux/12 hrs., 3-(p-methoxybenzoyl)amido-1-(2,4,6-trichlorophenyl)-2-pyrazolin-5-one, mp 216°–220° C., 49%.

EXAMPLE 17

2-[5-(2-Furyl)-1,2,4-oxadiazol-3-yl]-2',4',6'-trichloroacetanilide ($R^1=R^2=R^3=Cl$,

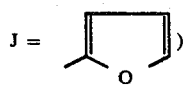

KOH/EtOH, reflux/4 hrs., 3-(2-furoylamido)-1-(2,4,6-trichlorophenyl)-2-pyrazolin-5-one, mp 240°–245° C. (dec.), 75%.

EXAMPLE 18

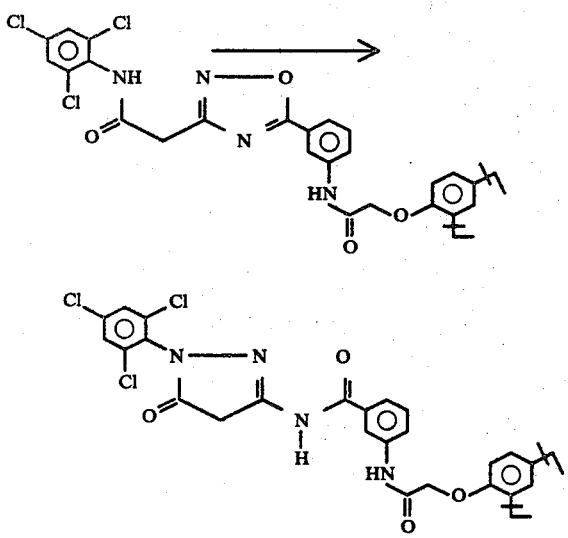

A mixture of 13.6 g of 2-[[5-{3-[(2,4-di-tert.-pentyl-phenoxy)acetamido]phenyl}-1,2,4-oxadiazol-3-yl]]-2',4',6'-trichloroacetanilide, 5.6 g of anhydrous potassium carbonate, and 25 ml of N,N-dimethylformamide (DMF) was heated at 110° C. with vigorous stirring for 2½ hours. The reaction mixture was poured into water and the precipitate was recrystallized twice from acetic acid and ethanol. There was obtained 9.0 g (68%) of 3-{[3-(2,4-di-tert.-pentylphenoxy)acetamido]benzoylamido}-1-(2,4,6-trichlorophenyl)-2-pyrazolin-5-one as colorless solid, mp 174.5°–178° C.

The same oxidazole did not give the desired 2-pyrazolin-5-one when the low-boiling protic solvent, anhydrous ethanol, was used instead of the high-boiling aprotic DMF, thus illustrating the preferability of higher temperatures and/or aprotic solvents for the practice of the invention.

EXAMPLE 19

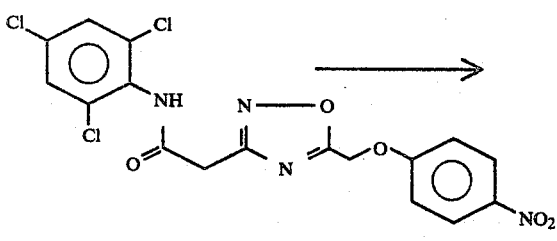

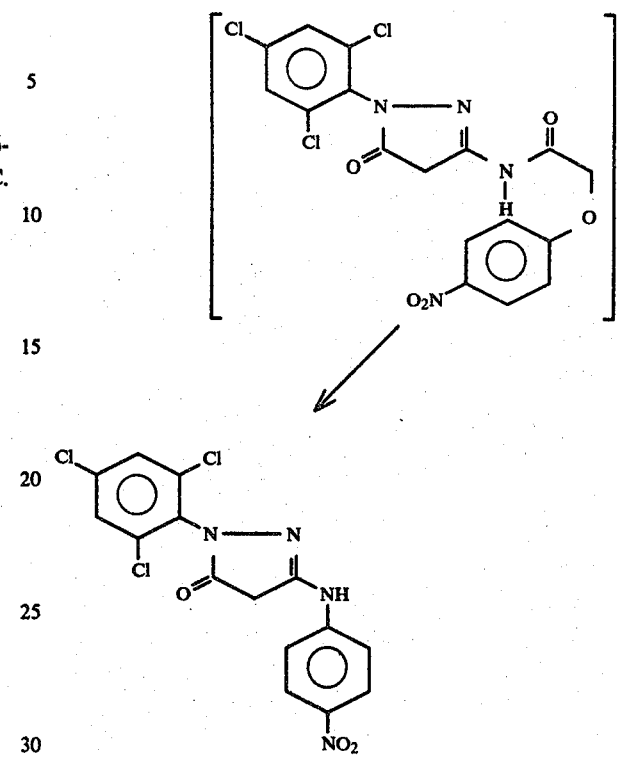

To a solution of 5 g of potassium hydroxide in 75 ml of anhydrous methanol was added 10 g of 2-[5-(p-nitrophenoxymethyl)-1,2,4-oxadiazol-3-yl]-2',4',6'-trichloroacetanilide. The mixture was heated under reflux for 2 hours. The reaction did not stop with 3-[(p-nitrophenoxy)acetamido]-1-(2,4,6-trichlorophenyl)-2-pyrazolin-5-one but proceeded further (Smiles rearrangement) to give 3-(p-nitroanilino)-1-(2,4,6-trichlorophenyl)-2-pyrazolin-5-one. At the end of the reaction, the mixture was allowed to cool to room temperature, acidified with 10 ml of acetic acid, diluted with 70 ml of water, and then allowed to stand at room temperature overnight. The product was collected, washed with water and ethanol, and dried. There was obtained 3.8 g (43%) of 3-(p-nitroanilino)-1-(2,4,6-trichlorophenyl)-2-pyrazolin-5-one as yellow crystals, mp 295°–298° C.

Examples 20–23 illustrate attempted rearrangements of oxadiazoles which are not within the scope of the invention. These examples illustrate the unexpected nature of the results of the practice of the present invention by showing that 1,2,4-oxadiazoles having certain substituent groups outside the scope of the invention are not converted to the corresponding 2-pyrazolin-5-ones by subjecting them to the reaction conditions of the method of the present invention.

EXAMPLES 20–23

The following compounds failed to give the corresponding 1-substituted-3-acylamino-2-pyrazolin-5-ones under any of the reaction conditions described in Examples 1–6.

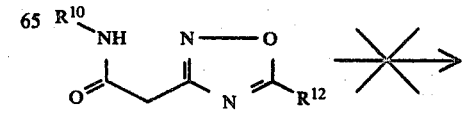

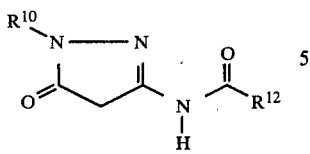

EXAMPLE 20

2-(5-Methyl-1,2,4-oxadiazol-3-yl)-4'-nitroacetanilide ($R^{10}$=p-$NO_2$—$C_6H_4$—, $R^{12}$=$CH_3$—).

EXAMPLE 21

N-Benzyl-2-(5-methyl-1,2,4-oxadiazol-3-yl)acetamide ($R^{10}$=phCH$_2$—, $R^{12}$=$CH_3$—).

EXAMPLE 22

2-[5-(p-Nitrophenyl)-1,2,4-oxadiazol-3-yl]-2',4',6'-trichloroacetanilide ($R^{10}$=2,4,6-$Cl_3$—$C_6H_2$—, $R^{12}$=p-$NO_2$—$C_6H_4$—).

EXAMPLE 23

2-[5-(m-Nitrophenyl)-1,2,4-oxadiazol-3-yl]-2',4',6'-trichloroacetanilide ($R^{10}$=2,4,6-$Cl_3$—$C_6H_2$—, $R^{12}$=m-$NO_2$—$C_6H_4$—.

This invention has been described in detail with particular reference to certain preferred embodiments thereof, but it will be understood that variations and modifications can be effected within the spirit and scope of the invention.

What is claimed is:

1. A method for preparing a 2-pyrazolin-5-one, which method comprises:
   (a) forming a substantially non-aqueous liquid reaction system comprising:
      (1) an organic liquid reaction medium,
      (2) a base catalyst, and
      (3) a 1,2,4-oxadiazole represented by the structural formula:

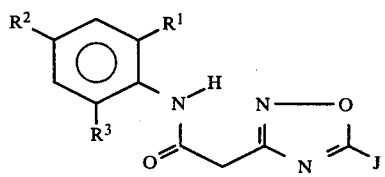

wherein each of $R^1$, $R^2$ and $R^3$ is hydrogen, halo, alkyl having from 1 to 5 carbon atoms, or alkoxy having from 1 to 5 carbon atoms; and J is alkyl having from 1 to 20 carbon atoms, phenoxyalkyl with the alkyl portion thereof having from 1 to 20 carbon atoms, phenyl, alkoxyphenyl, furyl, phenoxyacylaminophenyl, or phenoxyalkyl substituted with one or more nitro radicals in at least one of the para or ortho positions; and (b) heating said reaction system to a temperature sufficient to cause said 1,2,4-oxadiazole to rearrange to its corresponding 2-pyrazolin-5-one represented by the structural formula:

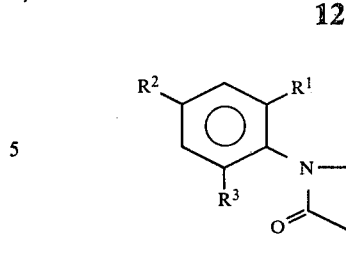

wherein $R^1$, $R^2$, $R^3$, and J are as defined hereinabove.

2. The method of claim 1, wherein said base catalyst is an alkali hydroxide, an alkali alkoxide, an alkali triphosphate, or an alkali carbonate.

3. The method of claim 1, wherein said organic liquid reaction medium is an aprotic organic solvent.

4. The method of claim 3 wherein said reaction system is heated to a temperature of at least 80° C. during said heating step and said base catalyst is an alkali hydroxide, an alkali alkoxide, an alkali triphosphate, or an alkali carbonate.

5. The method of claim 1, wherein said reaction system is heated to a temperature of from about 80° C. to about 125° C. during said heating step.

6. The method of claim 1, wherein said organic liquid reaction medium is a protic organic solvent and said reaction system is heated to a temperature of at least 80° C. during said heating step.

7. The method of claim 6 wherein said base catalyst is an alkali hydroxide, an alkali alkoxide, an alkali triphosphate or an alkali carbonate.

8. The method of claim 1, wherein said base catalyst is potassium hydroxide, sodium methoxide, or potassium carbonate.

9. The method of claim 1, wherein said organic liquid reaction medium is ethanol, methanol, 2-methoxyethanol, or N,N-dimethylformamide.

10. The method of claim 1, wherein said 1,2,4-oxadiazole is at least one of:
   (a) 2-(5-methyl-1,2,4-oxadiazol-3-yl)-2',4',6'-trichloroacetanilide;
   (b) 2-(5-methyl-1,2,4-oxadiazol-3-yl)acetanilide;
   (c) 2-{5-[1-(2,4-di-tert.-pentylphenoxy)-pentyl]-1,2,4-oxadiazol-3-yl}-2',4',6'-trichloroacetanilide;
   (d) 2-{5-[1-(m-pentadecylphenoxy)propyl]-1,2,4-oxadiazol-3-yl}-2',4',6'-trichloroacetanilide;
   (e) 2-{5-[1-(m-pentadecylphenoxy)propyl]-1,2,4-oxadiazol-3-yl}-2'-chloro-4',6'-dimethylacetanilide;
   (f) 2-(5-methyl-1,2,4-oxadiazol-3-yl)-4'-methoxyacetanilide;
   (g) 2-(5-ethyl-1,2,4-oxadiazol-3-yl)-2',4',6'-trichloroacetanilide;
   (h) 2-(5-n-propyl-1,2,4-oxadiazol-3-yl)-2',4',6'-trichloroacetanilide;
   (i) 2-(5-tert.-butyl-1,2,4-oxadiazol-3-yl)-2',4',6'-trichloroacetanilide;
   (j) 2-(5-phenyl-1,2,4-oxadiazol-3-yl)-2',4',6'-trichloroacetanilide;
   (k) 2-[5-(p-methoxyphenyl)-1,2,4-oxadiazol-3-yl]-2',4',6'-trichloroacetanilide;
   (l) 2-[5-(2-furyl)-1,2,4-oxadiazol-3-yl]-2',4',6'-trichloroacetanilide;
   (m) 2-[[5-{3-[(2,4-di-tert.-pentylphenoxy)acetamido]phenyl}-1,2,4-oxadiazol-3-yl]]-2',4',6'-trichloroacetanilide; or (n) 2-[5-(p-nitrophenoxymethyl)-1,2,4-oxadiazol-3-yl]-2',4',6'-trichloroacetanilide.

11. A method which comprises:
(a) forming a substantially non-aqueous liquid reaction system of a base catalyst and 2-[[5-{3-[2,4-di-tert.-pentylphenoxy)acetamido]phenyl}-1,2,4-oxadiazol-3-yl]]-2',4',6'-trichloroacetanilide in an aprotic organic solvent and
(b) heating said reaction system to a temperature sufficient to cause said 1,2,4-oxadiazole to be rearranged to form 3-{[3-(2,4-di-tert.-pentylphenoxy)acetamido]benzoylamido}-1-(2,4,6-trichlorophenyl)-2-pyrazolin-5-one.

12. The method of claim 11, wherein said base catalyst is an alkali hydroxide, an alkali alkoxide, an alkali triphosphate, or an alkali carbonate.

13. The method of claim 11, wherein said base catalyst is potassium hydroxide, sodium methoxide, or potassium carbonate.

14. The method of claim 11, wherein said aprotic organic solvent is N,N-dimethylformamide and said reaction system is heated to a temperature of about 110° C. during said heating step.

* * * * *